United States Patent
Martin Sanz et al.

(10) Patent No.: US 10,617,699 B2
(45) Date of Patent: Apr. 14, 2020

(54) ORAL FORMULATION FOR THE TREATMENT OF CARDIOVASCULAR DISEASES

(71) Applicants: FERRER INTERNACIONAL, S.A., Barcelona (ES); FUNDACIÓN CENTRO NACIONAL DE INVESTIGACIONES CARDIOVASCULARES CARLOS III, Madrid (ES)

(72) Inventors: Pablo Martin Sanz, Sant Cugat del Vallès (ES); Javier Urbano Hurtado, Sant Cugat del Vallès (ES)

(73) Assignees: FERRER INTERNACIONAL, S.A., Barcelona (ES); FUNDACIÓN CENTRO NACIONAL DE INVESTIGACIONES CARDIOVASCULARES CARLOS III, Madrid (ES)

( * ) Notice: Subject to any disclaimer, the term of this patent is extended or adjusted under 35 U.S.C. 154(b) by 0 days.

(21) Appl. No.: 14/893,902

(22) PCT Filed: Jun. 5, 2014

(86) PCT No.: PCT/EP2014/061735
§ 371 (c)(1),
(2) Date: Nov. 24, 2015

(87) PCT Pub. No.: WO2014/195421
PCT Pub. Date: Dec. 11, 2014

(65) Prior Publication Data
US 2016/0106763 A1    Apr. 21, 2016

(30) Foreign Application Priority Data
Jun. 6, 2013   (EP) .................................... 13170909

(51) Int. Cl.
*A61K 31/616* (2006.01)
*A61K 9/20* (2006.01)
(Continued)

(52) U.S. Cl.
CPC .......... *A61K 31/616* (2013.01); *A61K 9/2009* (2013.01); *A61K 9/2018* (2013.01);
(Continued)

(58) Field of Classification Search
CPC ...... A61K 9/2893; A61K 9/28; A61K 31/616; A61K 9/2018; A61K 9/2009;
(Continued)

(56) References Cited

U.S. PATENT DOCUMENTS

2003/0049314 A1   3/2003  Liang et al.
2007/0009591 A1   1/2007  Trivedi et al.
(Continued)

FOREIGN PATENT DOCUMENTS

EP    1 657 265 A1    5/2006
WO    WO 01/04195 A1  1/2001
(Continued)

OTHER PUBLICATIONS

"OPADRY Enteric", (Colorcon Application Data (2009), downloaded https://www.colorcon.com/literature/marketing/mr/Delayed%20Release/Opadry%20Enteric/Chinese/ads_opadry%20enteric_aspirin_FINAL_02.09.10.pdf, Feb. 17, 2016.*
(Continued)

*Primary Examiner* — Trevor Love
(74) *Attorney, Agent, or Firm* — Birch, Stewart, Kolasch & Birch, LLP (57) ABSTRACT

The present invention relates to an orally administrable pharmaceutical dosage form for use in the prevention and/or treatment of a cardiovascular disease which includes (a) acetylsalicylic acid as a first active agent and (b) HMG-CoA
(Continued)

reductase inhibitor as a second active agent. The HMG-CoA reductase inhibitor is selected from atorvastatin and rosuvastatin and salts thereof. The present invention is formulated in (a) two or more single separate coated dosage units in which the coating includes one or more water-soluble polymer and no more than 0 to 5% by weight of the coating of water-insoluble or enteric polymer, and in which the dosage units include 8 to 12 mg/cm2 coating and show an immediate release profile; and (b) one or more single separate coated dosage units.

16 Claims, 3 Drawing Sheets

(51) Int. Cl.
    *A61K 31/403*      (2006.01)
    *A61K 9/28*      (2006.01)
    *A61K 9/48*      (2006.01)
    *A61K 31/40*      (2006.01)
    *A61K 31/505*      (2006.01)

(52) U.S. Cl.
    CPC ............ *A61K 9/284* (2013.01); *A61K 9/4808* (2013.01); *A61K 31/40* (2013.01); *A61K 31/403* (2013.01); *A61K 31/505* (2013.01)

(58) Field of Classification Search
    CPC .... A61K 31/403; A61K 9/284; A61K 9/4804; A61K 31/40; A61K 31/505
    See application file for complete search history.

(56) References Cited

U.S. PATENT DOCUMENTS

| | | | |
|---|---|---|---|
| 2007/0116756 A1 | 5/2007 | Komireddi et al. | |
| 2007/0166375 A1 | 7/2007 | Patel et al. | |
| 2010/0092549 A1* | 4/2010 | Blundell | A61K 9/2072 424/456 |
| 2011/0086094 A1* | 4/2011 | Guerrero | A61K 9/2009 424/456 |
| 2012/0027849 A1 | 2/2012 | Khamar et al. | |
| 2012/0045505 A1 | 2/2012 | Sasmal et al. | |

FOREIGN PATENT DOCUMENTS

| | | |
|---|---|---|
| WO | WO 01/58429 A1 | 8/2001 |
| WO | WO 03/020243 A1 | 3/2003 |
| WO | WO 2004/080488 A2 | 9/2004 |
| WO | WO 2005/011586 A2 | 2/2005 |
| WO | WO 2006/000052 A1 | 1/2006 |
| WO | WO 2009/022821 A2 | 2/2009 |
| WO | WO 2009/118359 A2 | 10/2009 |
| WO | WO 2011/096665 A2 | 8/2011 |

OTHER PUBLICATIONS

"OPADRY amb" (Colorcon, Product Information Brouchure, (2009), downloaded from https://www.colorcon.com/literature/marketing/fc/Opadry%20amb/pib_opadry_amb.pdf, on Feb. 17, 2016.*
Buhler, Kollicoat Grades, BASF, 2007, pp. 7, 15, 16, 54, 55 and 59-65.*
International Search Report, dated Jul. 24, 2014, issued in PCT/EP2014/061735.
Annex 3 and 4 OPADRY amb product information filed by the Proprietor on Feb. 27, 2015, 5 pages.
European Office Action issued in European Patent Application No. 09 724 677.1 dated Mar. 22, 2012.
Feher et al., "Aspirin Resistance Possible Roles of Cardiovascular Risk Factors, Previous Disease History, Concomitant Medications and Haemorrheological Variables", Drugs and Aging, vol. 23 (2006) pp. 559-567.
International Preliminary Report on Patentability issued in PCT/EP2009/053545 dated Jul. 23, 2010.
Law et al., "Value of Low Dose Combination Treatment with Blood Pressure Lowering Drugs: Analysis of 354 Randomized Trials", British Medical Journal, vol. 326, No. 7404 (2003) pp. 1427-1431.
Levina et al., "The Influence of Formulation and Film Coating Systems on Stability of Ranitidine Tablets", AAPS Journal, vol. 5 (2004) p. S1.
Notice of Opposition issued in European Patent Application No. 14728940.9 dated Sep. 28, 2017.
Prosecution documents of International Application No. PCT/EP2009/053545 (published as WO2009118359 (D1)).
Schieffer et al., "Role of 3-Hydroxy-3-Methylglutaryl Coenzyme A Reductase Inhibitors, Angiotensin-Converting Enzyme Inhibitors, Cycloozygenase-2 Inhibitors, and Asprin in Anti-Inflammatory and Immunomodulatory Treatment . . . ", Amer J Cardio, vol. 91, No. 12 (suppl.1) (2003) pp. 12-18.
Experimental report with a comparison of the stability of 50 mg and 100 mg acetylsalicyclic acid film-coated tablets.
Experimental report with a dissollution profile comparison of 50 mg and 100 mg ASA film-coated tablets with a coating of 8.7 mg/cm2.
Polypill News: Apr. 2016 (https://www.world-heart-federation.org/polypill-news-april-2016/).
Response to Opposition for Appl. No. EP2986281 dated May 6, 2018.
European Patent Office Preliminary Opinion for EP Patent No. EP-B-2 986 281 dated Jul. 11, 2018.
Alexander, "Chapter 2: Dosage Forms and Their Routes of Administration," Pharmacology principles and practice, Elsevier, 2009, pp. 9, 18.
Brief Communication regarding oral Proceedings for European Application No. 14728940.9, dated Feb. 1, 2019.
Brief Communication regarding oral proceedings of Feb. 7, 2019, for European Application No. 14728940.9, dated Feb. 12, 2019.
Brief Communication regarding oral proceedings of Feb. 7, 2019, for European Application No. 14728940.9, dated Jan. 30, 2019.
Colorcon, "Opadry AMB White," Quantitative Formula, Mar. 23, 2005, 1 page.
Fegely et al., "OPADRY® amb/ OPADRY® II Application Data," Reprint of poster presented at AAPS, Oct. 2003, pp. 1-6.
Ho et al,. "Investigating Dissolution Performance Critical Areas on Coated Tablets: A Case Study Using Terahertz Pulsed Imaging," Journal of Pharmaceutical Sciences, vol. 99, No. 1, Jan. 1, 2010, pp. 392-402.
Information about the result of the oral proceedings of Feb. 7, 2019 for European Application No. 14728940.9.
Mollar, "Acetylsalicyclic Acid (ASA) 50 mg Film Coated Tablets: Dissolution Profile of Tablets with Different Film Coating Thickness," Jan. 24, 2019, 2 pages.
Qiu et al., "Developing Solid Oral Dosage Forms," Pharmaceutical Theory and Practice, Elsevier, 2009, p. 770 and 158 (4 pages total).
Rowe et al. (Ed.), "Polyvinyl Alcohol," Handbook of Pharmaceutical Excipients, Sixth Edition, 2009, pp. 564-565 (4 pages total).
Written Submission in preparation of oral proceedings dated Feb. 7, 2019, for European Application No. 14728940.9, dated Dec. 5, 2018.
Written Submission in preparation of oral proceedings of Feb. 7, 2019 for European Application No. 14728940.9, dated Jan. 24, 2019.
Written Submission in preparation of oral proceedings of Feb. 7, 2019, for European Application No. 14728940.9, dated Jan. 28, 2019.
Written Submission in preparation to oral proceedings of Feb. 7, 2019, for European Application No. 14728940.9, dated Feb. 6, 2019.
Written Submission to Opposition to European Patent EP2986281B1, European Application No. 14728940.9, dated Dec. 5, 2018.

* cited by examiner

ORAL FORMULATION FOR THE TREATMENT OF CARDIOVASCULAR DISEASES

FIELD OF THE INVENTION

The present invention relates to a pharmaceutical composition which includes a HMG-CoA reductase inhibitor, in particular, a statin and acetylsalicylic acid in a manner to minimize interaction of acetylsalicylic acid with the statin, for use in the prevention or treatment of cardiovascular diseases.

BACKGROUND OF THE INVENTION

Cardiovascular diseases are one of the leading causes of death in the world and one of the most significant factors for these diseases is total/high density lipoprotein (HDL) cholesterol level. However, recent developments have indicated that only taking the cholesterol level under control is not sufficient for cardiovascular treatment. In line with this need, researchers have found that the use of some active agents in combination provides a more effective treatment method.

The use of acetylsalicylic acid for reducing the risk of myocardial infarction and the use of statins for lowering cholesterol and preventing or treating cardiovascular disease and cerebrovascular disease are well documented. In fact, it is not uncommon that patients having elevated cholesterol levels who are at high risk for a myocardial infarction take both a statin and acetylsalicylic acid. However, use of both a statin and acetylsalicylic acid may require special care to insure that drug interaction, including physical and chemical incompatibility, and side effects, are kept to a minimum while achieving maximum benefit from these drugs.

HMG-CoA reductase inhibitors can be divided into two groups: those administered as a prodrug, i.e., the lactone form and those administered in the active form, i.e., the acid form or salts of the acid form (e.g. pravastatin sodium, atorvastatin calcium and rosuvastatin calcium). These compounds are unstable since they are susceptible to heat, moisture, low pH environment and light. Both atorvastatin and rosuvastatin and salts thereof, including calcium and magnesium salts, are particularly unstable when compared to other statins. In particular, atorvastatin is transformed into the lactone as a result of the intramolecular esterification reaction. Major degradation products (3R, 5S) produced as a result of disintegration of statins are lactones and oxidation products. This fact reduces the stability of atorvastatin and therefore shortens its shelf life.

It is known from the prior art that HMG-CoA reductase inhibitors degrade in the presence of acetylsalicylic acid during storage.

Document WO9738694 discloses pharmaceutical compositions comprising aspirin and a statin. However, the problem of statin-aspirin interaction is not addressed. Document EP1071403 addresses the problem of said interaction and describes a formulation in the form of a bilayered tablet. Aspirin, in the form of granules, is present in the first layer while the statin is present in the second layer. However, combination products produced in bilayer dosage forms can fail to prevent interaction of the active agents with each other. In this case, the product may be degraded during its shelf life. This may result in serious complications to the patient and insufficient dose intake.

Document EP 1581194 relates to multilayer tablet dosage form comprising pravastatin and aspirin as active agents. The layers comprising the active agents are separated by a barrier layer in order to impede their interaction. However, it is quite inconvenient to produce this type of tablet formulations and it is not certainly known if the barrier layer would maintain its effect during the shelf life.

Document WO2011096665 describes that the deterioration in the stability of HMG-CoA reductase can be prevented by coating aspirin with a barrier containing a hydrophobic additive. According to said document, when aspirin is coated with conventional coatings, HMG-CoA reductase inhibitors are degraded. When a hydrophobic additive is added to the coating layer, the degradation of HMG-CoA reductase inhibitors is reduced.

In view of the above, it is seen that there is a need in patients required to take both a statin and acetylsalicylic acid for a statin-acetylsalicylic acid formulation which provides for maximum effect in cardiovascular diseases prevention and treatment without the undesirable side effects and drug interaction normally associated with use of such combination.

In accordance with the present invention, a pharmaceutical composition is provided which includes a HMG-CoA reductase inhibitor selected from atorvastatin and rosuvastatin and salts thereof, and acetylsalicylic acid, which provides for maximum patient benefits with minimal physical and chemical incompatibility and reduced side effects normally associated with use of such drugs.

SUMMARY OF THE INVENTION

The authors of the present invention have found that when acetylsalicylic acid is provided in an oral formulation and the amount of coating for acetylsalicylic acid units is above 6 mg/cm$^2$ and said coating contains a water-soluble polymer, the deterioration in the stability of atorvastatin and rosuvastatin can be surprisingly prevented.

Thus, the present invention refers to an orally administrable pharmaceutical dosage form for use in the prevention and/or treatment of a cardiovascular disease comprising:
(a) acetylsalicylic acid as a first active agent; and
(b) HMG-CoA reductase inhibitor as a second active agent, wherein said HMG-CoA reductase inhibitor is selected from atorvastatin and rosuvastatin and salts thereof, and wherein
(a) are two or more single separate coated dosage units comprising one or more water-soluble polymer in said coating and being said coating substantially free from a water-insoluble polymer or an enteric polymer; and wherein the amount of coating is above 6 mg/cm2; and showing a non-modified release profile; and
(b) is one or more single separate coated dosage units; and the dosage units are selected from the group consisting of tablets, particles, granules, pellets and capsules.

DETAILED DESCRIPTION OF THE INVENTION

The pharmaceutical dosage form of the present invention exhibits improved storage stability of HMG-CoA reductase inhibitors atorvastatin and rosuvastatin (and salts thereof) in the presence of acetylsalicylic acid, thereby providing useful combinations for the prevention and treatment of cardiovascular diseases.

The authors of the present invention have developed a new formulation. This new formulation consists of an oral dosage form containing separate coated dosage units for each drug substance, being said units tablets, particles, granules or pellets and being the amount of coating for acetylsalicylic acid units above standard levels. In fact, the authors of the present invention have found that when the amount of coating for acetylsalicylic acid units is above 6 mg/cm² and said coating contains a water-soluble polymer, the deterioration in the stability of atorvastatin or rosuvastatin can be surprisingly prevented. As it is shown in the examples below, the production of lactone H, which is the major degradation product of atorvastatin, is significantly lower in the formulation of the invention when compared to a formulation containing a standard coating.

Thus, in a first aspect, the present invention refers to an orally administrable pharmaceutical dosage form for use in the prevention and/or treatment of a cardiovascular disease comprising:
(a) acetylsalicylic acid as a first active agent; and
(b) HMG-CoA reductase inhibitor as a second active agent, wherein said HMG-CoA reductase inhibitor is selected from atorvastatin and rosuvastatin and salts thereof, and wherein (a) are two or more single separate coated dosage units comprising one or more water-soluble polymer in said coating and being said coating substantially free from a water-insoluble polymer or an enteric polymer; and wherein the amount of coating is above 6 mg/cm2; and showing a non-modified release profile; and
(b) is one or more single separate coated dosage units; and the dosage units are selected from the group consisting of tablets, particles, granules, pellets and capsules.

As used herein the term "dosage units" refers to dosage forms containing a single dose or a part of a dose of drug substance in each unit. According to the present invention, said dosage units can be in the form of tablets, particles, granules, pellets or capsules.

Multiple dosage forms of the present invention can be prepared by combining one or more dosage units in an oral formulation. These dosage units can be tablets, granules, pellets, capsules or particles or combinations thereof. As it can be understood by the skilled person in the pharmaceutical industry, the term "granulation" refers to the act or process in which primary powder particles are made to adhere to form larger, multiparticle entities called granules. Thus, it is the process of collecting particles together by creating bonds between them. Bonds are formed by compression or by using a binding agent. Granulation is extensively used in the manufacturing of tablets and pellets (or spheroids).

As used herein the term "tablet" includes tablets, mini tablets or micro tablets. Similarly, the term "capsule" also can refer to micro capsules. Suitable capsules may be either hard or soft, and are generally made of gelatin, starch, or a cellulosic material, gelatin capsules being preferred. Two-piece hard gelatin capsules are preferably sealed by gelatin bands or the like. In a preferred embodiment, said orally administrable pharmaceutical dosage form according to the invention is in the form of a capsule. In another preferred embodiment, wherein (a) and/or (b) dosage units are in the form of tablets.

The term "cardiovascular disease" as used herein refers to a disease such as hypercholesterolemia, atherosclerosis, coronary and cerebral diseases, for instance myocardial infarction, secondary myocardial infarction, myocardial ischemia, angina pectoris, congestive heart diseases, cerebral infarction, cerebral thrombosis, cerebral ischemia and temporary ischemic attacks.

The compositions of the present invention may be used as treatment for acute cardiovascular events, as well as for chronic therapy for prevention or reduction of risk of occurrence of cardiovascular events.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. Thus, for example, "treating" a patient involves prevention of a particular disorder or adverse physiological event in a susceptible individual as well as treatment of a clinically symptomatic individual.

As used herein, the terms "aspirin" or "acetylsalicylic acid (ASA)" are used interchangeably.

This invention employs effective cholesterol-lowering agents that are HMG CoA reductase inhibitors. HMG-CoA reductase inhibitors can be divided into two groups: those administered as the prodrug, i.e., the lactone form and those administered in the active form, i.e., the acid form (e.g. atorvastatin and rosuvastatin).

Compounds which have inhibitory activity for HMG-CoA reductase can be readily identified by using assays well-known in the art. For example, see the assays described or cited in U.S. Pat. No. 4,231,938 at col. 6, and WO 84/02131 at pp. 30-33.

The HMG-CoA reductase inhibitor for use in the formulation of the invention is selected from atorvastatin and rosuvastatin and salts thereof, in particular calcium and magnesium salts.

The term "HMG-CoA reductase inhibitor" is intended to include all pharmaceutically acceptable salt or ester of the compounds having HMG-CoA reductase inhibitory activity according to the invention, and therefore the use of such salts or esters is included within the scope of this invention.

The expression "pharmaceutically acceptable salts" includes both pharmaceutically acceptable acid addition salts and pharmaceutically acceptable cationic salts. The expression "pharmaceutically-acceptable cationic salts" is intended to define but is not limited to such salts as the alkali metal salts, (e.g. sodium and potassium), alkaline earth metal salts (e.g. calcium and magnesium), aluminum salts, ammonium salts, and salts with organic amines such as benzathine (N,N'-dibenzylethylenediamine), choline, diethanolamine, ethylenediamine, meglumine (N-methylglucamine), benethamine (N-benzylphenethylamine), diethylamine, piperazine, tromethamine (2-amino-2-hydroxymethyl-1,3-propanediol) and procaine. The expression "pharmaceutically-acceptable acid addition salts" is intended to define but is not limited to such salts as the hydrochloride, hydrobromide, sulfate, hydrogen sulfate, phosphate, hydrogen phosphate, dihydrogenphosphate, acetate, succinate, citrate, methanesulfonate (mesylate) and p-toluenesulfonate (tosylate) salts. It will also be recognized that it is possible to administer amorphous forms of the statins.

The pharmaceutically-acceptable cationic salts of statins containing free carboxylic acids may be readily prepared by reacting the free acid form of the statin with an appropriate base, usually one equivalent, in a co-solvent. Typical bases are sodium hydroxide, sodium methoxide, sodium ethoxide, sodium hydride, potassium methoxide, magnesium hydroxide, calcium hydroxide, benzathine, choline, diethanolamine, piperazine and tromethamine. The salt is isolated by concentration to dryness or by addition of a non-solvent. In many cases, salts are preferably prepared by mixing a solution of the acid with a solution of a different salt of the cation (sodium or potassium ethylhexanoate, magnesium oleate), employing a solvent (e.g., ethyl acetate) from which the desired cationic salt precipitates, or can be otherwise isolated by concentration and/or addition of a non-solvent.

The pharmaceutically acceptable acid addition salts of statins containing free amine groups may be readily prepared by reacting the free base form of the statin with the appropriate acid. When the salt is of a monobasic acid (e.g., the hydrochloride, the hydrobromide, the p-toluenesulfonate, the acetate), the hydrogen form of a dibasic acid (e.g., the hydrogen sulfate, the succinate) or the dihydrogen form of a tribasic acid (e.g., the dihydrogen phosphate, the citrate), at least one molar equivalent and usually a molar excess of the acid is employed. However when such salts as the sulfate, the hemisuccinate, the hydrogen phosphate or the phosphate are desired, the appropriate and exact chemical equivalents of acid will generally be used. The free base and the acid are usually combined in a co-solvent from which the desired salt precipitates, or can be otherwise isolated by concentration and/or addition of a non-solvent.

A number of mechanisms are likely responsible for the cardiovascular protective activity of acetylsalicylic acid, but its antithrombotic, anti-platelet aggregating activities are probably highly significant in this regard. Acetylsalicylic acid irreversibly acetylates the enzyme cyclooxygenase, rendering it nonfunctional. Cyclooxygenase is essential for the synthesis of (among other compounds) prostaglandins, many of which are proinflammatory; thromboxane A2, which is synthesized by platelets to promote platelet aggregation and ultimately thrombosis (blood clotting); and prostacyclins, which have anti-platelet aggregating properties. Cyclooxygenases are synthesized in endothelial cells and not in platelets. Low doses of acetylsalicylic acid neutralize cyclooxygenase selectively in the platelets, while allowing continued cyclooxygenase and prostacyclin synthesis in the endothelial cells. The net effect is to reduce inflammation and platelet aggregation, and thus thrombosis, in the blood vessels.

As mentioned above, when the amount of coating for each acetylsalicylic acid dosage unit is above 6 mg/cm$^2$ and said coating comprises a water-soluble polymer, the deterioration in the stability of HMG-CoA reductase inhibitor, in particular, atorvastatin and rosuvastatin, is surprisingly reduced. Moreover, as it is shown in the Examples accompanying the present invention, a dosage form according to the present invention comprising acetylsalicylic acid in the form of two dosage units, wherein the amount of coating for said acetylsalicylic acid units is above 6 mg/cm$^2$, has the effect of reducing the amount of atorvastatin impurities produced in addition to maintaining a non-modified release profile for the acetylsalicylic acid dosage units.

As used herein, the amount of coating expressed in mg/cm$^2$ refers to the amount of coating per cm$^2$ of surface of the core of active ingredient. In a particular embodiment of the invention, the amount of coating for acetylsalicylic acid dosage units is comprised from 6 to 12 mg/cm$^2$, more particularly, the amount of coating for acetylsalicylic acid dosage units is comprised from 7 to 11 mg/cm$^2$. In a preferred embodiment, the amount of coating for acetylsalicylic acid dosage units is comprised from 8 to 10 mg/cm$^2$.

According to the present invention, acetylsalicylic acid dosage units (a) have a non-modified or conventional release profile. According to another particular embodiment, all dosage units in the formulation of the invention have non-modified or conventional release profile.

As used herein the terms "conventional release" or "non-modified release" profile are used indistinctively and it is to be understood as pertaining a dosage form showing a release of the active substance(s) which is not deliberately modified by a special formulation design and/or manufacturing method. In the case of a solid dosage form the dissolution profile of the active substance depends essentially on its intrinsic properties. It is also understood that non-modified or conventional release is, essentially, immediate release of active ingredients. This is further understood to be traditional or conventional release profile where no slow, delayed or extended release effect is incorporated. Preferably, means that a percentage equal to or greater than 65% of the active ingredient is dissolved within 60 minutes, preferably within 30 minutes and more preferably within 15 minutes in a US Pharmacopeia type 1 apparatus in 0.05 M acetate buffer, at pH 4.5, 100 rpm in a volume of 900 ml. More preferably the percentage of active ingredient dissolved is greater than 75%, more preferably greater than 80%.

The term "water-soluble polymer" as used herein refers to a wide range of highly varied families of products of natural or synthetic origin. These polymers are often used as thickeners, stabilizers, film formers, rheology modifiers, emulsifiers and lubricity aids. Basically, water soluble polymers are highly hydrophilic as a result of the presence of oxygen and nitrogen atoms: hydroxyl, carboxylic acid, sulfonate, phosphate, amino, imino groups etc. Examples of suitable water soluble polymers according to the present invention include, for instance, water soluble cellulose derivatives such as hydroxypropyl methylcellulose, hydroxypropyl cellulose, hydroxyethyl cellulose, hydroxylethylmethyl cellulose carboxymethylcellulose calcium or sodium, methylcellulose or combinations thereof, sugars such as glucose, fructose or polydextrose, polyalcohols such as sorbitol, mannitol, maltitol, xylitol and isomalt, maltodextrin, polyethylene oxide, povidone, copovidone, gelatine, partly hydrolyzed polyvinyl alcohol, polyvinyl alcohol, poloxamer, or combinations thereof. In a particular embodiment of the invention, said the water-soluble polymer is selected from the group consisting of a water-soluble cellulose ether selected from methylcellulose, hydroxypropylcellulose and hydroxypropylmethylcellulose and mixtures thereof; a water-soluble polyvinyl derivative selected from polyvinyl pyrrolidone, partly hydrolyzed polyvinyl alcohol and polyvinyl alcohol and mixtures thereof; an alkylene oxide polymer selected from polyethylene glycol and polypropylene glycol; and mixtures thereof.

In a preferred embodiment, said water soluble polymer is present in an amount by weight above 40% of the total weight of the coating. In another preferred embodiment, said water soluble polymer is selected from hydroxypopyl methylcellulose, partly hydrolyzed polyvinyl alcohol and polyvinyl alcohol or a mixture thereof.

According to the present invention, the acetylsalicylic acid dosage unit coating is substantially free from a water-insoluble polymer or an enteric polymer. The term "substantially free" as used here in refers to the presence of the substance (s) to which it refers, i.e. a water-insoluble polymer or an enteric polymer, in amounts ranging between 0 to 5% b.w., more preferably in amounts ranging between 0 to 1% by weight of the composition of the coating. In a preferred embodiment, said coating contains no more than about 0.1% by weight of the composition of the coating of a water-insoluble polymer or enteric polymer.

Examples of water-insoluble polymers include waxes such as carnauba wax, glyceryl monostearate, glyceryl monooleate and beeswax; and synthetic or semisynthetic hydrophobic polymers such as ethyl cellulose, aminoalkyl methacrylate copolymer RS, ethyl acrylate-methyl methacrylate copolymer, polyvinyl chloride, polyvinyl acetate and cellulose acetate.

As it is known in the art, acetylsalicylic acid can lead to stomach diseases in long-term use. Thus, according to the present invention, acetylsalicylic acid units can optionally comprise an enteric coating layer. Said coating layer would preferably be included between the acetylsalicylic acid core and the water-soluble polymer coating. Enteric or gastroresistant coating is intended to resist the gastric fluid and to release the active substance or substances in the intestinal fluid.

Coating materials that can be used in enteric coating of said dosage forms can be selected from methacrylic copolymers for instance methacrylic acid/methyl methacrylate, methacrylic acid/ethyl acrylate copolymers, methacrylic acid/methyl acrylate/methyl methacrylate copolymers, shellac, hydroxypropyl methylcellulose phthalate, hydroxyl propyl methyl cellulose acetate succinate, hydroxypropyl methyl cellulose trimellitate, cellulose acetate phthalates, polyvinyl acetate phthalates or combinations thereof. Commonly used plasticizers as may be suitable for particular enteric polymers can be used. It will be appreciated that any polymer with suitable plasticizer can be used in aqueous or non-aqueous system to form an enteric coating on the acetylsalicylic acid dosage unit. The coating can, and usually does, contain a plasticizer to prevent the formation of pores and cracks that would permit the penetration of the gastric fluids.

Enterically coated dosage forms may be manufactured using standard enteric coating procedures and equipment. For example, an enteric coating can be applied using a coating pan, an airless spray technique, fluidized bed coating equipment, or the like.

In addition to the active agent(s), the dosage units of the formulation of the invention prepared for oral administration will generally contain other pharmaceutically acceptable excipients such as binders, diluents, lubricants, disintegrants, fillers, stabilizers, surfactants, coloring agents, and the like. The terms "pharmaceutically acceptable excipients", "pharmaceutically compatible excipients", and "excipients" are used interchangeably in this disclosure. They refer to non-API substances such as binders, diluents, lubricants, disintegrants, fillers, stabilizers, surfactants, coloring agents, and the like used in formulating pharmaceutical products. They are generally safe for administering to humans according to established governmental standards.

Binders are used to impart cohesive qualities to a dosage form. Suitable binder materials include, but are not limited to, starch (including corn starch and pregelatinized starch), gelatin, sugars (including sucrose, glucose, dextrose, and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, ethyl cellulose, hydroxyethyl cellulose, and the like), and water-washed smectite clays such as Veegum®.

Diluents are typically used to increase bulk so that a practical size dosage unit, for example a tablet, is ultimately obtained. Suitable diluents include alkali metal carbonates, cellulose derivatives (microcrystalline cellulose, cellulose acetate, etc.), phosphates, maltodextrin, dextrin, fructose, dextrose, glyceryl palmitostearate, lactitol, lactose, including direct compression lactose, maltose, mannitol, sorbitol, starch, talc, xylitol and/or hydrates thereof and/or derivatives thereof.

Examples of suitable lubricants include, for example, metallic stearates (such as magnesium stearate, calcium stearate, aluminum stearate), fatty acid esters (such as sodium stearyl fumarate), fatty acids (such as stearic acid), fatty alcohols, glyceryl behenate, mineral oil, paraffins, hydrogenated vegetable oil, leucine, polyethylene glycols (PEG), metallic lauryl sulfate (such as sodium lauryl sulfate, magnesium lauryl sulfate), sodium chloride, sodium benzoate, sodium acetate, talc, siliconized talc and/or hydrates thereof.

Disintegrants used in the present invention enable the dosage form to disperse in water easily and rapidly. Disintegrants can be selected from a group comprising polymers having high dispersing characteristics such as cross-linked hydroxypropyl cellulose, polyvinylpyrrolidone, high molecular weight polymers, microcrystalline cellulose, sodium starch glycolate, croscarmellose sodium, crospovidone; the products known under the trademarks Kollidon® CL, Polyplasdone® or alginic acid, sodium alginate, corn starch.

Basic agents of the present invention are either water-soluble or water-insoluble and selected from a group comprising meglumine, trometamol, sodium bicarbonate, sodium carbonate, sodium citrate, calcium gluconate, disodium hydrogen phosphate, dipotassium hydrogen phosphate, tripotassium phosphate, sodium tartrate, sodium acetate, calcium glycerophosphate, magnesium oxide, magnesium hydroxide, aluminum hydroxide, dihydroxy aluminum, sodium carbonate, calcium carbonate, aluminum carbonate, dihydroxy aluminum amino acetate, diethanolamine, triethanolamine, N-methyl-glucamine, glucosamine, ethylenediamine, triethyleneamine, isopropylamine, di-isopropyl amine or combinations thereof.

Stabilizers are used to inhibit or retard drug decomposition reactions that include, by way of example, oxidative reactions.

Surfactants may be anionic, cationic, amphoteric, or nonionic surface-active agents. Surfactants that can optionally be used in the present invention are selected from a group comprising sodium lauryl sulfate, dioctyl sulfosuccinate, gelatin, casein, lecithin, dextran, sorbitan esters, polyoxy ethylene alkyl ethers, polyethylene glycols, polyethylene stearates, collodial silicon dioxide.

Anti-adhesive agents can be used in the present invention in order to prevent the mixture comprising active agents to adhere onto device and machine surfaces and create rough surfaces. The substances used for this purpose can comprise one or more components selected from a group comprising talc, colloidal silicone dioxide (Aerosil, Syloid, Cab-OSil), magnesium stearate and corn starch.

Release rate determinant polymers that can be used in the formulations of the present invention can be pH-dependant polymers, non pH-dependant polymers, swellable polymers, non-swellable polymers, hydrophilic polymers, hydrophobic polymers and/or one or more hydrophobic substances;

ionic polymers such as sodium alginate, carbomer, calcium carboxy methyl cellulose or carboxy methyl cellulose; non-ionic polymers such as hydroxy propyl methyl cellulose; natural or/synthetic polysaccharides such as alkyl celluloses, hydroxyl alkyl celluloses, cellulose ethers, nitrocellulose, dextrin, agar, carrageenan, pectin, starch and starch derivatives or mixtures thereof; cellulosic polymers; methacrylate polymers, methacrylate copolymers, polyvinylpyrrolidone, polyvinylpyrrolidone-polyvinyl acetate copolymer, ethyl cellulose, cellulose acetate, cellulose propionate (high, medium and low molecular weight), cellulose acetate propionate, cellulose acetate butyrate, cellulose acetate phthalate, cellulose triacetate, polyvinyl acetate, polyvinyl chloride and mixtures thereof.

As mentioned above, acetylsalicylic acid dosage units (a) show a non-modified or conventional release profile. However, release rate determinant polymers as the ones mentioned in the paragraph above, can also be used in the dosage form of the present invention for the other dosage units. Therefore, the dosage units according to the invention may show a modified release profile. The term "modified release" as used herein includes all types of modified release profiles such as controlled release, sustained release, delayed release, and the like.

The film coating materials of the present invention can contain the following components and/or combinations thereof: lactose, hydroxypropyl methyl cellulose, hydroxypropyl cellulose, triacetine, hydroxypropyl methyl cellulose phthalate, hydroxypropyl methyl cellulose acetate phthalate, polyvinyl acetate phthalate, diethyl phthalate, sugar derivatives, polyvinyl derivatives, waxes, fats and gelatins, triethyl citrate, glyceride, titanium oxide, talc, sodium alginate, stearic acid, lecithin.

The term "therapeutically effective amount" as used herein is intended to mean that amount of a drug or pharmaceutical agent that will elicit the biological or medical response of a tissue, a system, animal or human that is being sought by a researcher, veterinarian, medical doctor or other clinician. The dosage regimen utilizing an HMG-CoA reductase inhibitor in combination with acetylsalicylic acid will be selected in accordance with a variety of factors including type, species, age, weight, sex and medical condition of the patient; the severity of the condition to be treated; the route of administration; the renal and hepatic function of the patient; and the particular compound or salt or ester thereof employed. Since two or more different active agents are being used together in a combination therapy, the potency of each of the agents and the enhanced effects achieved by combining them together must also be taken into account. A consideration of these factors is well within the purview of the ordinarily skilled clinician for the purpose of determining the therapeutically effective amounts of the drug combination needed to prevent, counter, or arrest the progress of the condition.

In a particular embodiment of the invention the amount of acetylsalicylic acid in the formulation is in the range of 10-400 mg per dosage unit. More preferable, the amount of acetylsalicylic acid is in the range of 30-100 mg per dosage unit. In a more preferred embodiment, the amount of acetylsalicylic acid per dosage unit is in the range of 40-85, more preferably 40-60 mg per dosage unit, even more preferably 50 mg.

The pharmaceutical dosage form of the invention will contain a HMG-CoA reductase inhibitor, in particular a statin selected from atorvastatin and rosuvastatin and salts thereof in an amount as normally employed for such statin. Thus, depending upon the particular statin, it may be employed in amounts within the range from about 0.1 mg to 2000 mg per day in single or divided doses, and preferably from about 0.2 to about 200 mg per day. The clinical dosage range for atorvastatin is 10-80 mg per day. Therefore, in a particular embodiment of the invention the amount of HMG-CoA reductase inhibitor in the dosage form of the invention can be in the range of 1-40 mg per dosage unit, more preferably, from 5-40, even more preferably from 5-20 mg per dosage unit. In a preferred embodiment of the invention, the HMG-CoA reductase inhibitor is in the form of two or more dosage units in the dosage form of the invention.

In a particular embodiment of the invention, the composition further comprises one or more single separate dosage units comprising an inhibitor of the rennin-angiotensin system as a third active agent.

The renin aldosterone angiotensin system (RAAS) plays an important role in the regulation of blood pressure and volume homeostasis, and pivotal roles in the pathophysiology of cardiovascular, renal, and metabolic diseases. Renin is secreted by the kidney in response to a decrease in circulating volume and blood pressure, and cleaves the substrate angiotensinogen to form the inactive decapeptide angiotensin I (Ang I). Ang I is converted to the active octapeptide angiotensin II (Ang II) by angiotensin converting enzyme (ACE). Ang II interacts with cellular receptors, in particular ATI receptors, inducing vasoconstriction and release of catecholamines from the adrenal medulla and pre-junctional nerve endings. It also promotes aldosterone secretion and sodium reabsorption. In addition, Ang II inhibits renin release, thus providing a negative feedback to the system. Accordingly, Ang II acts at various levels (e.g. vasculature, sympathetic nervous system, cortex and medulla of the adrenal gland) to increase vascular resistance and blood pressure.

The RAAS can be blocked at various levels. Renin inhibitors, ACE inhibitors (ACEi) and angiotensin receptor blockers (ARBs) represent major drug classes that block the RAAS. Each individual drug class has a different mode of action and thus blocks the RAAS at a different level: Renin inhibitors block the first, rate-limiting step of RAAS cascade by competitively inhibiting the enzyme renin, thereby preventing the formation of Ang I from angiotensinogen. ACEi block the second step of the RAAS cascade by competitively inhibiting the enzyme ACE, thereby preventing the formation of Ang II. Finally, ARBs block the third and last step of the RAAS cascade by binding to and occupying the ATI receptors without activating them. Thereby, ARBs prevent binding and activation of said ATI receptors by Ang II. It has been disclosed that certain gene polymorphisms reflecting on cardiovascular systems are useful as biomarkers for predicting disease susceptibility or progression, or as a guide for individualized therapy, including drug therapy.

The renin inhibitors to which the present invention applies are any of those having renin inhibitory activity in vivo. Renin inhibitors for use herein include, but are not limited to, those disclosed in EP 678.503, WO 00/64887, WO 00/064873, WO 2005/051895, WO 2006/095020, US 2009/0076062, WO 2011/056126, Yokokawa et al. (Expert Opin. Ther. Patents 18(6):581-602, 2008), and Maibaum et al. (Expert Opin. Ther. Patents 13(5):589-603, 2003). Moreover, suitable renin inhibitors include compounds having different structural features. In one embodiment, the renin inhibitor is preferably selected from aliskiren, ditekiren, terlakiren, zankiren, RO 66-1132, RO 66-1168, VTP27999, ACT-280778, and TAK-272, and pharmaceutically acceptable salts, prodrugs, derivatives and isomers thereof.

An ARB according to the invention is any molecule that can specifically antagonize or block the action of angiotensin II type 1 receptors (ATI receptors). ARBs suitable for use herein include, but are not limited to, losartan, valsartan, irbesartan, candesartan, telmisartan, eprosartan, tasosartan, zolarsartan, azilsartan, olmesartan, saprisartan, forasartan, E-4177, and ZD-8731, and pharmaceutically acceptable salts, prodrugs, derivatives and isomers thereof.

In a preferred embodiment, the inhibitor of the rennin-angiotensin system is an angiotensin-converting enzyme (ACE) inhibitor. An ACEi according to the invention is any molecule that can specifically inhibit the enzymatic activity of angiotensin converting enzyme. ACEi suitable for use herein include, but are not limited to, benazepril, benazeprilat, captopril, zofenopril, enalapril, enaprilat, fosinopril, ceronapril, lisinopril, moexipril, perindopril, quinapril, ramipril, trandolapril, alacepril, cilazapril, delapril, imidapril, rentiapril, spirapril, temocapril, and moveltipril, and pharmaceutically acceptable salts, prodrugs, derivatives and isomers thereof. In one embodiment, the preferred ACEi is ramipril and pharmaceutically acceptable salts thereof.

Ramipril is a prodrug, which is rapidly hydrolysed after absorption to the active metabolite ramiprilat. Ramipril and ramiprilat inhibit angiotensin-converting enzyme (ACE). ACE is a peptidyl dipeptidase that catalyzes the conversion of angiotensin I to the vasoconstrictor substance, angiotensin II. Angiotensin II also stimulates aldosterone secretion by the adrenal cortex. Inhibition of ACE results in decreased plasma angiotensin II, which leads to decreased vasopressor activity and to decreased aldosterone secretion. The latter decrease may result in a small increase of serum potassium. The effect of ramipril on hypertension appears to result at least in part from inhibition of both tissue and circulating ACE activity, thereby reducing angiotensin II formation in tissue and plasma. Administration of ramipril to patients with mild to moderate hypertension results in a reduction of both supine and standing blood pressure to about the same extent with no compensatory tachycardia. Symptomatic postural hypotension is infrequent, although it can occur in patients who are salt- and/or volume-depleted. Ramipril can significantly reduce the incidence of MI, stroke or death from cardiovascular causes in patients aged > or =55 years who are at increased risk for the development of ischaemic cardiovascular events.

In a particular embodiment of the invention, the ACE inhibitor dosage units have an unmodified release profile. In another particular embodiment, said ACE inhibitor is in the form of one or more single separate dosage units selected from the group consisting of tablets, particles, granules, pellets and capsules. In a preferred embodiment, said dosage units are coated dosage units.

On average, the daily dose of ramipril in a patient weighing approximately 75 kg is at least 0.001 mg/kg, preferably 0.01 mg/kg, to about 20 mg/kg, preferably 1 mg/kg, of body weight. In a particular embodiment of the invention, the amount of ramipril in said formulation is in the range of 1-100 mg per dosage unit, more preferably in the range of 2-50 mg per dosage unit.

The following examples are put forth so as to provide those of ordinary skill in the art with a complete disclosure and description of how to make and use the present invention, and are not intended to limit the scope of the invention or to represent that the experiments below are all or the only experiments performed. Efforts have been made to ensure accuracy with respect to numbers used (e.g., amounts, temperature, and the like), but some experimental errors and deviations may be present.

EXAMPLES

Film-coated tablets comprising acetylsalicylic acid (ASA), atorvastatin and ramipril were manufactured and encapsulated (AAR capsules).

As mentioned above, different film-forming polymers can be used according to the present invention. The term PVA as used herein refers to a partly hydrolyzed polyvinyl alcohol.

Manufacture of Atorvastatin Coated Tablets

Atorvastatin tablets were manufactured by wet granulation using a high shear mixer and fluid bed dryer. Granulation solution was prepared dispersing polysorbate 80 and hydroxypropyl cellulose in purified water. The intragranular components (see Table 2) were incorporated to the blend to be granulated. Finally, the extragranular components (see Table 2) were added and blended with the obtained granules. Each blend was compressed in a rotary press machine. After tabletting, cores obtained were film coated.

Manufacture of ASA Coated Tablets

Acetylsalicylic acid, sodium starch glycolate and microcrystalline cellulose were sieved in the appropriate proportions (see Table 5) and blended. The talc (lubricant) was sieved and blended with the previously obtained blend and the final blend compressed. The resulting core was coated with the aqueous film-forming solution.

Atorvastatin (10 mg or 20 mg) and ASA (40.5; 50 mg or 100 mg) film coated tablets were manufactured as described above and encapsulated along with ramipril (2.5, 5 or 10 mg) film coated tablets. Ramipril film coated tablets are commercially available.

The composition of the manufactured capsules was as follows:

TABLE 1

Composition of AAR capsules

| Component | Example 1 AAR capsules (tablet/capsule) | Example 2 AAR capsules (tablet/capsule) |
| --- | --- | --- |
| ASA 100 mg film coated tablets | 1 | |
| ASA 50 mg film coated tablets | — | 2 |
| Atorvastatin 10/20 mg film coated tablets | 2 | 2 |
| Ramipril 10 mg film coated tablets | 1 | 1 |

TABLE 2 atorvastatin 10 mg film-coated tablets composition

| Component | (mg/tablet) |
| --- | --- |
| Intragranular | |
| atorvastatin calcium trihydrate[(1)] | 10.845 |
| lactose monohydrate | 36.805 |
| pregelatinised starch | 21.000 |
| calcium carbonate | 29.600 |
| hydroxypropylcellulose | 3.000 |
| Polysorbate 80 | 1.000 |
| purified water [(2)] | 22.000 |
| total (mg) | 102.25 |
| Extragranular | |
| crospovidone | 6.000 |
| silica colloidal anhydrous | 1.000 |
| magnesium stearate | 0.750 |
| total (mg) | 110.000 |

TABLE 2-continued atorvastatin 10 mg film-coated tablets composition

| Component | (mg/tablet) |
|---|---|
| Film coating | |
| Hydroxypropylmethyl cellulose coating | 3.300 |
| purified water [2] | 22.000 |
| Total (mg) | 113.300 |

[1] Equivalent to 10 mg atorvastatin. Atorvastatin calcium trihydrate purity is corrected with lactose monohydrate.
[2] Removed during manufacturing process

TABLE 3 atorvastatin 20 mg film-coated tablets intragranular composition

| Component | (mg/tablet) |
|---|---|
| Intragranular | |
| atorvastatin calcium trihydrate[1] | 21.690 |
| lactose monohydrate | 35.360 |
| pregelatinised starch | 21.000 |
| calcium carbonate | 49.200 |
| hydroxypropylcellulose | 3.000 |
| Polysorbate 80 | 2.000 |
| purified water [2] | 27.000 |
| total (mg) | 132.250 |
| Extragranular | |
| Crospovidone | 6.000 |
| silica colloidal anhydrous | 1.000 |
| magnesium stearate | 0.750 |
| total (mg) | 140.000 |
| Film coating | |
| Hydroxypropylmethyl cellulose coating | 4.200 |
| purified water [2] | 28.000 |
| Total (mg) | 144.200 |

[1] Equivalent to 20 mg atorvastatin. Atorvastatin calcium trihydrate purity is corrected with lactose monohydrate.
[2] Removed during manufacturing process

TABLE 4 composition of 100 mg, 50 mg and 40.5 mg ASA film-coated tablets

| COMPOSITION | FUNCTION | QUANTITY (mg) | QUANTITY (mg) | QUANTITY (mg) |
|---|---|---|---|---|
| acetylsalicylic acid | active ingredient | 100.0 | 50.0 | 40.50 |
| sodium starch glycolate | disintegrant | 3.75 | 7.50 | 7.10 |
| microcrystalline cellulose | diluent | 20.00 | 41.50 | 51.00 |
| talc | lubricant | 1.25 | 1.00 | 1.00 |
| TOTAL: | | 125.00 | 100.00 | 100.00 |

In the finished product film coated tablets of atorvastatin were placed inside a capsule along with film coated tablets of ramipril and film coated tablets of acetylsalicylic acid (ASA).

In order to improve the stability of the formulation, a partly hydrolyzed polyvinyl alcohol, was used as film forming agent for acetylsalicylic acid (ASA) tablets. Different amounts of film coating for ASA tablets were tested: 2.17 mg/cm$^2$, 4.3 mg/cm$^2$ and 8.7 mg/cm$^2$.

TABLE 5 composition of PVA coating

| Component | w/w % |
|---|---|
| partially hydrolysed polyvinyl alcohol | 45.50 |
| titanium dioxide | 30.00 |
| Talc | 22.00 |
| soy lecithin | 2.00 |
| xanthan gum | 0.50 |
| Total | 100.00 |

Presence of atorvastatin impurities in capsules comprising ASA film-coated tablets (one tablet of 100 mg ASA or 2×50 mg) under different stress conditions (40° C., 30° C., and 25° C.) was tested.

As it is shown in Table 6, in all cases (40° C., 30° C., and 25° C.) aspirin tablets with 8.7 mg/cm$^2$ coating, yielded lower levels of lactone H than tablets with 4.3 mg/cm$^2$ coating (standard level).

TABLE 6

Atorvastatin impurities when ASA is coated with different thickness of PVA coatings (4.3 mg/cm$^2$ and 8.7 mg/cm$^2$):

| | | Initial | 40° C. 3 months | 30° C. 3 months | 25° C. 3 months |
|---|---|---|---|---|---|
| Example 1 AAR capsules: | | | | | |
| ASA, 100 mg 4.3 mg/cm$^2$ | | | | | |
| ASA Assay Impurities | | 100.2 | 100.6 | 98.6 | 100.1 |
| | Salycilic acid | 0.05 | 0.71 | 0.28 | 0.12 |
| | Total impurities | 0.05 | 0.76 | 0.35 | 0.19 |
| ATV Assay Impurities | | 98.7 | 100.5 | 99.9 | 101.9 |
| | Impurity D | 0.10 | 0.09 | 0.09 | 0.09 |
| | Impurity H | 0.10 | 0.57 | 0.43 | 0.41 |
| | Total impurities | 0.20 | 0.79 | 0.55 | 0.53 |
| Example 2 AAR capsules: | | | | | |
| ASA 50 mg x2 8.7 mg/cm$^2$ | | | | | |
| ASA Assay Impurities | | 97.6 | 101.3 | 97.7 | 98.7 |
| | Salycilic acid | 0.09 | 0.19 | 0.13 | 0.18 |
| | Total impurities | 0.19 | 0.32 | 0.18 | 0.33 |
| ATV Assay Impurities | | 99.5 | 97.4 | 96.8 | 98.3 |
| | Impurity D | 0.05 | 0.06 | 0.05 | 0.06 |
| | Impurity H | 0.08 | 0.15 | 0.05 | 0.08 |
| | Total impurities | 0.22 | 0.58 | 0.30 | 0.47 |

Dissolution Profile of ASA Tablets 50 mg or 40.5 mg strength formulations of ASA tablets (see Table 4) were prepared in order to check whether the dissolution rate could be improved by reducing the strength of the formulations.

TABLE 7

Comparative dissolution rate of 100 mg
and 50 mg ASA strength formulations

| | | FORMULATION | |
|---|---|---|---|
| PARAMETER | UNITS | 100 mg RESULTS | 50 mg (x2) RESULTS |
| Dissolution test (0.05M Acetate buffer pH 4.5; 50 rpm; 500 ml) | minutes, % | 5 Mean = 38% CV = 23.44% 15 Mean = 96% CV = 5.32% 30 Mean = 99% CV = 2.84% | 5 Mean = 58% CV = 8.52% 15 Mean = 103% CV = 3.21% 30 Mean = 105% CV = 3.09% |

Dissolution tests were performed under the following conditions: 0.05 M acetate buffer pH 4.5; 50 rpm US Pharmacopeia type 1 apparatus; 500 ml.

Figure 1:
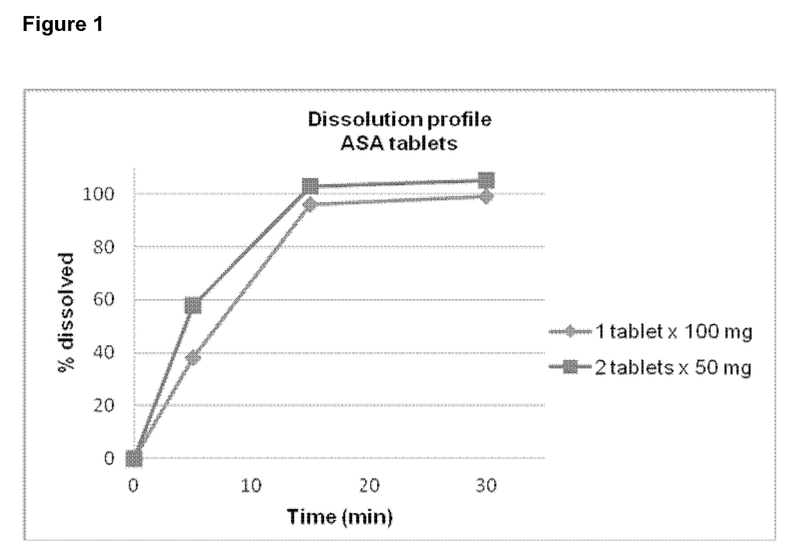
FIG. 1 represents the dissolution profiles of 100 mg and 50 mg ASA strength formulations (4.3 mg/cm$^2$ coating).

Dissolution data showed (See FIG. 1 and Table 7) an improvement in dissolution profile of the ASA tablets when the strength of the formulation is reduced.

Dissolution rate of two tablets of acetylsalicylic acid 50 mg is faster than one of acetylsalicylic acid 100 mg.

Next step was to test if similar results are obtained when using film-coated tablets. The effect of PVA coating in the dissolution profile of film-coated tablets of 50 mg ASA compared to 100 mg ASA tablets was tested. Different amounts of film coating agent were tested: 2.17 mg/cm$^2$, 4.3 mg/cm$^2$ and 8.7 mg/cm$^2$.

Figure 2:
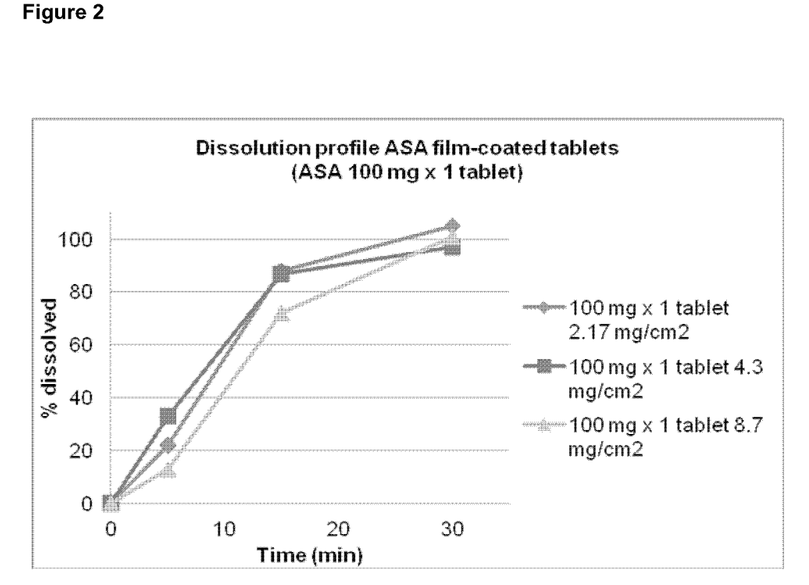
FIG. 2 shows the dissolution profile of acetylsalicylic acid 100 mg tablets containing different amounts of film coating agent per cm$^2$ (2.17, 4.3 and 8.7).

As it is shown in Table 8 and FIG. 2, by increasing the amount of coating by more than 4.3 mg/cm2, the dissolution profile of the 100 mg ASA tablets is affected. Mean values of % dissolved at 15 minutes are over 85% in ASA tablets comprising 2.17 mg/cm$^2$ and 4.3 mg/cm$^2$ coating. However, said value is below 75% in tablets comprising 8.7 mg/cm$^2$ coating.

Dissolution Test Conditions:
Apparatus: USP 1 (basket)
Stirring speed: 50 rpm
Dissolution Volume: 500 mL
Dissolution media: pH 4.5 acetate buffer

TABLE 8

ASA 100 mg film-coated tablets (PVA coating) dissolution results

| Time (min) | ASA 100 mg film-coated tablets 2.17 mg/cm$^2$ | ASA 100 mg film-coated tablets 4.3 mg/cm$^2$ | ASA 100 mg film-coated tablets 8.7 mg/cm$^2$ |
|---|---|---|---|
| 0 | 0 | 0 | 0 |
| 5 | 22 | 33 | 13 |
| 15 | 88 | 87 | 72 |
| 30 | 105 | 97 | 101 |

However, as it is shown in Table 9, 50 mg ASA tablets comprising 8.7 mg/cm$^2$ coating do not show any negative effect on the dissolution profile, as at 15 minutes mean values of % dissolved are over 85%.

TABLE 9

2x50 mg ASA PVA coated tablets dissolution results

| Time (min) | ASA 50 mg film-coated tablets 2.17 mg/cm2 | ASA 50 mg film-coated tablets 4.3 mg/cm2 | ASA 50 mg film-coated tablets 8.7 mg/cm2 |
|---|---|---|---|
| 0 | 0 | 0 | 0 |
| 5 | 41 | 47 | 33 |
| 15 | 94 | 96 | 101 |
| 30 | 101 | 106 | 115 |

Figure 3:
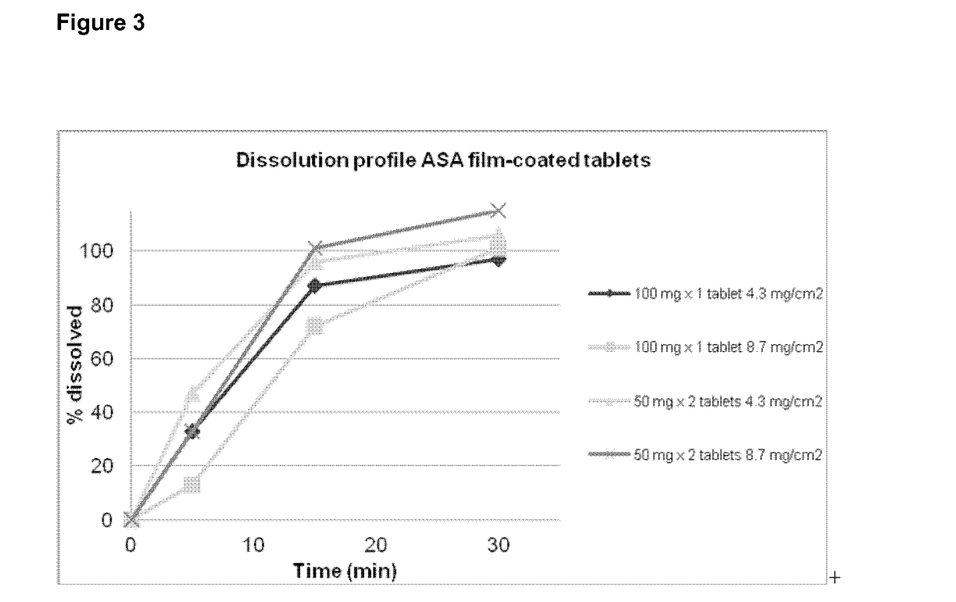
FIG. 3 shows the dissolution profile of 50 mg versus 100 mg ASA tablets containing 4.3 and 8.7 mg/cm$^2$ of film coating agent.

Dissolution results (see FIG. 3; Tables 11 and 12) show that the dissolution rate of 2 tablets of 50 mg ASA is in all cases (2.17 mg/cm$^2$, 4.3 mg/cm$^2$ and 8.7 mg/cm$^2$) faster than that of one tablet of 100 mg ASA. Also, comparing the dissolution profile of 50 mg tablets and 100 mg tablets with 4.3 mg/cm$^2$ and 8.7 mg/cm$^2$ coating, it can be observed that 50 mg (2×) tablets with 8.7 mg/cm$^2$ coating dissolve faster than 100 mg tablets with 4.3 mg/cm$^2$ coating.

Figure 4:
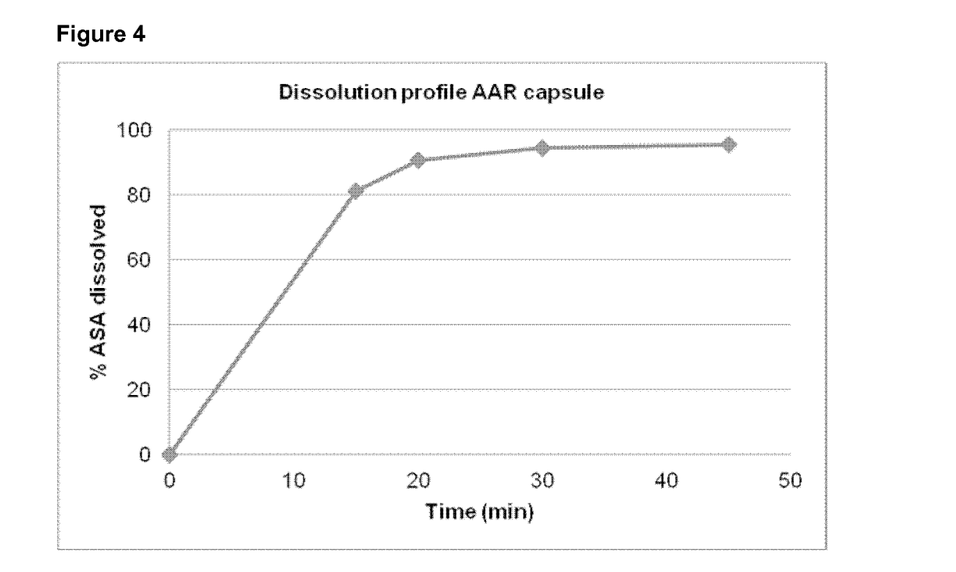
FIG. 4 shows the dissolution profile of AAR capsules containing ASA 50 mg×2 film-coated tablets with 8.7 mg/cm$^2$ at pH 4.5.

Dissolution profiles of AAR capsules containing ASA 50 mg×2 film-coated tablets with 8.7 mg/cm$^2$ were also performed at different conditions:

Dissolution Test Conditions:
Apparatus: USP 1 (basket)
Stirring speed: 100 rpm
Dissolution Volume: 900 mL
Dissolution media: pH 4.5 acetate buffer
Results (Table 10 and FIG. 4) were as follows:

TABLE 10

% ASA dissolved in AAR capsules dissolution results

| Time (min) | AAR capsule % ASA dissolved |
|---|---|
| 0 | 0 |
| 15 | 81.3 |
| 20 | 90.7 |
| 30 | 94.4 |
| 45 | 95.5 |

Figure 5:
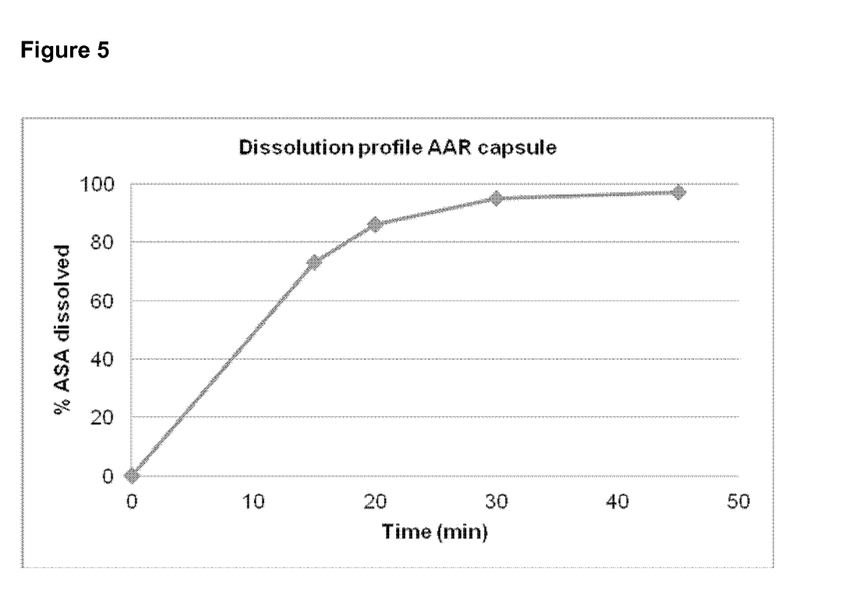
FIG. 5 shows the dissolution profile of AAR capsules containing ASA 50 mg×2 film-coated tablets with 8.7 mg/cm² at pH 6.8.

Dissolution Test Conditions:
Apparatus: USP 1 (basket)
Stirring speed: 100 rpm
Dissolution Volume: 900 mL
Dissolution media: pH 6.8 phosphate buffer
Results (Table 11 and FIG. 5) were as follows:

TABLE 11

% ASA dissolved in AAR capsules dissolution results

| Time (min) | AAR capsule % ASA dissolved |
|---|---|
| 0 | 0 |
| 15 | 73.1 |
| 20 | 86.2 |
| 30 | 95.3 |
| 45 | 97.3 |

As shown in Table 10 and Table 11, AAR capsule containing 50 mg ASA film-coated tablets×2, comprising 8.7 mg/cm$^2$ of tablet coating, show mean values over 80% at 15 minutes in the case of pH 4.5 and close to 75% at pH 6.8.

A formulation comprising ASA tablets with 8.7 mg/cm$^2$ coating provides more protection and isolation to the acetylsalicylic acid tablet, making more difficult that salicylic acid can sublime and it can trigger the degradation of the other components, in particular, of atorvastatin or rosuvastatin inside the final capsule.

The invention claimed is:

1. An orally administrable pharmaceutical dosage form comprising:
   (a) acetylsalicylic acid as a first active agent; and
   (b) HMG-CoA reductase inhibitor as a second active agent, wherein said HMG-CoA reductase inhibitor is atorvastatin or salts thereof, and wherein
(a) is formulated in two or more single separate coated dosage units showing an immediate release profile, wherein the coating comprises one or more water-soluble polymer and less than or equal to 5% of water-insoluble and enteric polymers by weight of the coating; and wherein the dosage units comprise an amount of coating of 8 to 12 mg per cm$^2$ of surface of a core of the active agent; and
(b) is formulated in one or more single separate coated dosage units;
   the dosage units are in the form of tablets, and
   the water soluble polymer is present in an amount by weight above 40% of the total weight of the coating and is a water-soluble polyvinyl derivative comprising at least one or more of polyvinyl pyrrolidone, partly hydrolyzed polyvinyl alcohol or polyvinyl alcohol.

2. The pharmaceutical dosage form according to claim 1, wherein said dosage form is in the form of a capsule.

3. The pharmaceutical dosage form according to claim 1, wherein the water-soluble polymer is partly hydrolyzed polyvinyl alcohol, polyvinyl alcohol, and mixtures thereof.

4. The pharmaceutical dosage form according to claim 1, wherein acetylsalicylic acid dosage units (a) show a percentage equal to or greater than 65% of acetylsalicylic acid dissolved within 60 minutes in a US Pharmacopeia type 1 apparatus in 0.05 M acetate buffer, at pH 4.5, 100 rpm in a volume of 900 ml.

5. The pharmaceutical dosage form according to claim 1, wherein the amount of acetylsalicylic acid in said dosage form is in the range of 10 to 400 mg per dosage unit.

6. The pharmaceutical dosage form according to claim 1, wherein the amount of HMG-CoA reductase inhibitor in said dosage form is in the range of 5 to 40 mg per dosage unit.

7. The pharmaceutical dosage form according to claim 1, wherein the HMG-CoA reductase inhibitor is in the form of two or more dosage units.

8. The pharmaceutical dosage form according to claim 1, further comprising one or more single separate dosage units comprising an inhibitor of the rennin-angiotensin system as a third active agent.

9. The pharmaceutical dosage form according to claim 8, wherein the inhibitor of the rennin-angiotensin system is at least one ACE inhibitor selected from the group consisting of ramipril, captopril, cilazapril, delapril, enalapril, fentiapril, fosinopril, indolapril, lisinopril, perindopril, pivopril, quinapril, spirapril, trandolapril, zofenopril and pharmaceutically acceptable salts, or
   wherein the inhibitor of the rennin-antiotensin system is at least one angiotensin receptor blocker selected from the group consisting of losartan, valsartan, irbesartan, candesartan, telmisartan, eprosartan, tasosartan, zolarsartan, azilsartan, olmesartan, saprisartan, forasartan, E-4177, ZD-8731, and pharmaceutically acceptable salts.

10. Pharmaceutical dosage form according to claim 9, wherein said ACE inhibitor is ramipril or pharmaceutically acceptable salts.

11. The pharmaceutical dosage form according to claim 4, wherein acetylsalicylic acid dosage units (a) show a percentage equal to or greater than 75% of acetylsalicylic acid dissolved within 60 minutes in a US Pharmacopeia type 1 apparatus in 0.05 M acetate buffer, at pH 4.5, 100 rpm in a volume of 900 ml.

12. The pharmaceutical dosage form according to claim 4, wherein acetylsalicylic acid dosage units (a) show a percentage equal to or greater than 80% of acetylsalicylic acid dissolved within 60 minutes in a US Pharmacopeia type 1 apparatus in 0.05 M acetate buffer, at pH 4.5, 100 rpm in a volume of 900 ml.

13. The pharmaceutical dosage form according to claim 4, wherein acetylsalicylic acid dosage units (a) show a percentage equal to or greater than 85% of acetylsalicylic acid dissolved within 60 minutes in a US Pharmacopeia type 1 apparatus in 0.05 M acetate buffer, at pH 4.5, 100 rpm in a volume of 900 ml.

14. The pharmaceutical dosage form according to claim 4, wherein acetylsalicylic acid dosage units (a) show a percentage equal to or greater than 85% of acetylsalicylic acid dissolved within 30 minutes in a US Pharmacopeia type 1 apparatus in 0.05 M acetate buffer, at pH 4.5, 100 rpm in a volume of 900 ml.

15. The pharmaceutical dosage form according to claim 4, wherein acetylsalicylic acid dosage units (a) show a percentage equal to or greater than 85% of acetylsalicylic acid dissolved within 15 minutes in a US Pharmacopeia type 1 apparatus in 0.05 M acetate buffer, at pH 4.5, 100 rpm in a volume of 900 ml.

16. The pharmaceutical dosage form according to claim 1, wherein acetylsalicylic acid dosage units (a) show a percentage equal to or greater than 80% of acetylsalicylic acid dissolved from within 20 to 30 minutes in a US Pharmacopeia type 1 apparatus in 0.05 M acetate buffer, at pH 4.5, 100 rpm in a volume of 900 ml.

* * * * *